US00PP15367P2

(12) United States Plant Patent
Bloom et al.

(10) Patent No.: US PP15,367 P2
(45) Date of Patent: Nov. 23, 2004

(54) ***POLEMONIUM* PLANT NAMED 'POLBRESS'**

(50) Latin Name: *Polemonium hybrida*
Varietal Denomination: Polbress

(75) Inventors: Adrian Bloom, Diss (GB); Paul Gooderham, Diss (GB)

(73) Assignee: Blooms of Bressingham Ltd., Bressingham (GB)

( * ) Notice: Subject to any disclaimer, the term of this patent is extended or adjusted under 35 U.S.C. 154(b) by 0 days.

(21) Appl. No.: 10/602,092

(22) Filed: Jun. 23, 2003

(51) Int. Cl.[7] ..... A01H 5/00
(52) U.S. Cl. ..... Plt./263
(58) Field of Search ..... Plt./263

*Primary Examiner*—Kent Bell
*Assistant Examiner*—Louanne Krawczewicz Myers
(74) *Attorney, Agent, or Firm*—C. A. Whealy

(57) ABSTRACT

A distinct cultivar of *Polemonium* plant named 'Polbress', characterized by its upright plant habit; strong and erect flowering stems; purple-colored foliage; freely flowering habit; and light violet blue-colored flowers with bright yellow-colored anthers.

2 Drawing Sheets

Botanical classification/cultivar designation: *Polemonium hybrida* cultivar Polbress.

BACKGROUND OF THE INVENTION

The present Invention relates to a new and distinct cultivar of *Polemonium* plant, botanically known as *Polemonium hybrida*, and hereinafter referred to by the cultivar name 'Polbress'.

The new *Polemonium* originated from a cross-pollination in 1995 of the *Polemonium* cultivar Purple Rain, not patented, as the female, or seed, parent with an unindentified selection of *Polemonium yezoense*, not patented, as the male, or pollen, parent. The cultivar Polbress was discovered and selected by the Inventors as a flowering plant within the progeny of the stated cross-pollination in a controlled environment in June, 1996 in Bressingham, Diss, Norfolk, United Kingdom.

Asexual reproduction of the new cultivar by divisions and basal cuttings taken at Bressingham, Diss, Norfolk, United Kingdom, since April, 1997, has shown that the unique features of this new *Polemonium* are stable and reproduced true to type in successive generations.

SUMMARY OF THE INVENTION

Plants of the cultivar Polbress have not been observed under all possible environmental conditions. The phenotype may vary somewhat with variations in environment such as temperature and light intensity without, however, any variance in genotype.

The following traits have been repeatedly observed and are determined to be the unique characteristics of 'Polbress'. These characteristics in combination distinguish 'Polbress' as a new and distinct cultivar:

1. Upright plant habit; strong and erect flowering stems.
2. Purple-colored foliage.
3. Freely flowering habit.
4. Light violet blue-colored flowers with bright yellow-colored anthers.

Plants of the new *Polemonium* are most similar to plants of the female parent, the cultivar Purple Rain. In side-by-side comparisons conducted in Bressingham, Diss, Norfolk, United Kingdom, plants of the new *Polemonium* differed from plants of the cultivar Purple Rain in the following characteristics:

1. Plants of the new *Polemonium* were taller and broader than plants of the cultivar Purple Rain.
2. Plants of the new *Polemonium* had larger leaves than plants of the cultivar Purple Rain.
3. Fully expanded leaves of plants of the new *Polemonium* were purple in color whereas fully expanded leaves of plants of the cultivar Purple Rain were light green flushed with purple.
4. Plants of the new *Polemonium* were more freely flowering than plants of the cultivar Purple Rain.
5. Plants of the new *Polemonium* had taller inflorescences than plants of the cultivar Purple Rain.
6. Flowering stems of plants of the new *Polemonium* were more erect than the flowering stems of plants of the cultivar Purple Rain.

Plants of the new *Polemonium* can also be compared to plants of the male parent selection. In side-by-side comparisons conducted in Bressingham, Diss, Norfolk, United Kingdom, plants of the new *Polemonium* differed from plants of the male parent selection in the following characteristics:

1. Plants of the new *Polemonium* were taller than and not as spreading as plants of the male parent selection.
2. Fully expanded leaves of plants of the new *Polemonium* were purple in color whereas fully expanded leaves of plants of the male parent selection were green in color.
3. Flowers of plants of the new *Polemonium* were more violet in color than plants of the male parent selection.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Polemonium*.

The photograph on the first sheet comprises a side perspective view of typical plants of 'Polbress' grown in the landscape.

The photograph on the second sheet is a close-up view of typical inflorescences of 'Polbress'.

DETAILED BOTANICAL DESCRIPTION

In the following description, color references are made to The Royal Horticultural Society Colour Chart, 1995 Edition, except where general terms of ordinary dictionary significance are used. Plants were grown in Bressingham, United Kingdom under outdoor field conditions which closely approximate commercial production conditions. During the production of the plants, day temperatures ranged from 5 to 28° C. and night temperatures ranged from −8 to 15° C. Plants used for the description were grown for two growing seasons in 5-liter containers.

Botanical classification: *Polemonium hybrida* cultivar Polbress.

Parentage:

*Female, or seed, parent.*—*Polemonium hybrida* cultivar Purple Rain not patented.

*Male, or pollen, parent.*—Unidentified selection of *Polemonium yezoense*, not patented.

Propagation:

*Type.*—By basal cuttings.

*Time to initiate roots.*—About 10 days at 20° C.

*Time to produce a rooted cutting.*—About 20 days at 20° C.

*Root description.*—Fibrous, thin, brownish white in color.

*Rooting habit.*—Freely branching, dense.

Plant description:

*Plant form.*—Upright and freely basal clumping perennial; dense and bushy plants; leaves, basal; flowering stems arise from the root crown.

*Plant height, soil level to top of flowers.*—About 70 cm.

*Plant width.*—About 45 cm.

*Foliage description.*—Arrangement: Opposite, compound; about 25 leaflets per leaf. Leaf length: About 4.5 cm. Leaf width: About 1.5 cm. Leaflet length: About 7.5 mm. Leaflet width: About 2.5 mm. Leaflet shape: Lanceolate. Leaflet apex: Acute. Leaflet base: Cuneate. Leaflet margin: Entire. Leaflet texture, upper and lower surfaces: Slightly pubescent. Leaflet venation pattern: Lacinate. Leaflet color: Developing foliage, upper surface: 137D flushed with 79A. Developing foliage, lower surface: 137A flushed with 79D. Fully expanded foliage, upper surface: 79B. Fully expanded foliage, lower surface: 79C to 79D. Venation, upper surface: 79A. Venation, lower surface: 138B. Leaf petiole length: About 5 cm. Leaf petiole diameter: About 2 mm. Leaf petiole color: 179B.

Flower description:

*Flower type and habit.*—Single flowers arranged on corymbose racemes on long basal flowering stems. Flowering stems, mostly erect; flowers outwardly drooping. Flowers not persistent.

*Fragrance.*—Faint.

*Natural flowering season.*—Flowering continuous from June to July in Bressingham, Diss, Norfolk, United Kingdom.

*Quantity.*—Freely flowering with about 20 flowers and flower buds per flowering stem.

*Flower longevity.*—About five days on the plant.

*Inflorescence height.*—About 30 cm.

*Inflorescence diameter.*—About 10 cm.

*Flower diameter.*—About 3 cm.

*Flower depth (height).*—About 1.5 cm.

*Flower buds.*—Length: About 5 mm. Diameter: About 3 mm. Shape: Ovoid. Color: 155A.

*Petals.*—Quantity/arrangement: About five or six petals fused at the base, imbricate. Length: About 1.5 cm. Width: About 1 cm. Shape: Orbicular. Apex: Rounded. Margin: Entire. Texture, upper and lower surfaces: Smooth; satiny. Color: When opening, upper surface: 92A. When opening, lower surface: 92A; towards the base, 83A. Fully opened, upper surface: 92A; color becoming closer to 92B to 92C. Fully opened, lower surface: 92B.

*Sepals.*—Quantity/arrangement: About six fused into a tube. Length: About 6 mm. Diameter: About 3 mm. Shape: Lanceolate. Apex: Acute. Margin: Entire. Texture, upper and lower surfaces: Smooth, satiny. Color: When opening, upper surface: 137B flushed with 90A. When opening, lower surface: 137C flushed with 90B. Fully opened, upper surface: 90C flushed with 137B. When opening, lower surface: 90C flushed with 137C.

*Flowering stems.*—Strength: Strong. Angle: Erect. Texture: Sparsely pubescent. Color: 79B.

*Peduncles.*—Length: About 2 cm. Diameter: About 1 mm. Strength: Strong. Angle: Acute. Texture: Smooth, glabrous. Color: 79B.

*Pedicels.*—Length: About 7 mm. Diameter: About 1 mm. Strength: Strong. Angle: Acute. Texture: Smooth, glabrous. Color: 79B.

*Reproductive organs.*—Stamens: Quantity per flower: About five. Anther length: About 4 mm. Anther shape: Obovate. Anther color: 13A. Pollen amount: Sparse. Pollen color: 13A. Pistils: Quantity per flower: One. Style length: About 1 cm. Style color: 92A. Stigma shape: Narrow tubular. Stigma color: 92A. Ovary color: 144B.

*Seed.*—Length: About 4 mm. Diameter: About 1 mm. Color: 166A.

Disease/pest resistance: Under commercial production conditions, plants of the new *Polemonium* have not been noted to be resistant to pathogens or pests common to *Polemonium*.

Weather/temperature tolerance: Plants of the new *Polemonium* have been observed to tolerate rain, wind, and temperatures from −8 to 28° C. in Bressingham, Diss, Norfolk, United Kingdom.

It is claimed:

1. A new and distinct cultivar of *Polemonium* plant named 'Polbress', as illustrated and described.

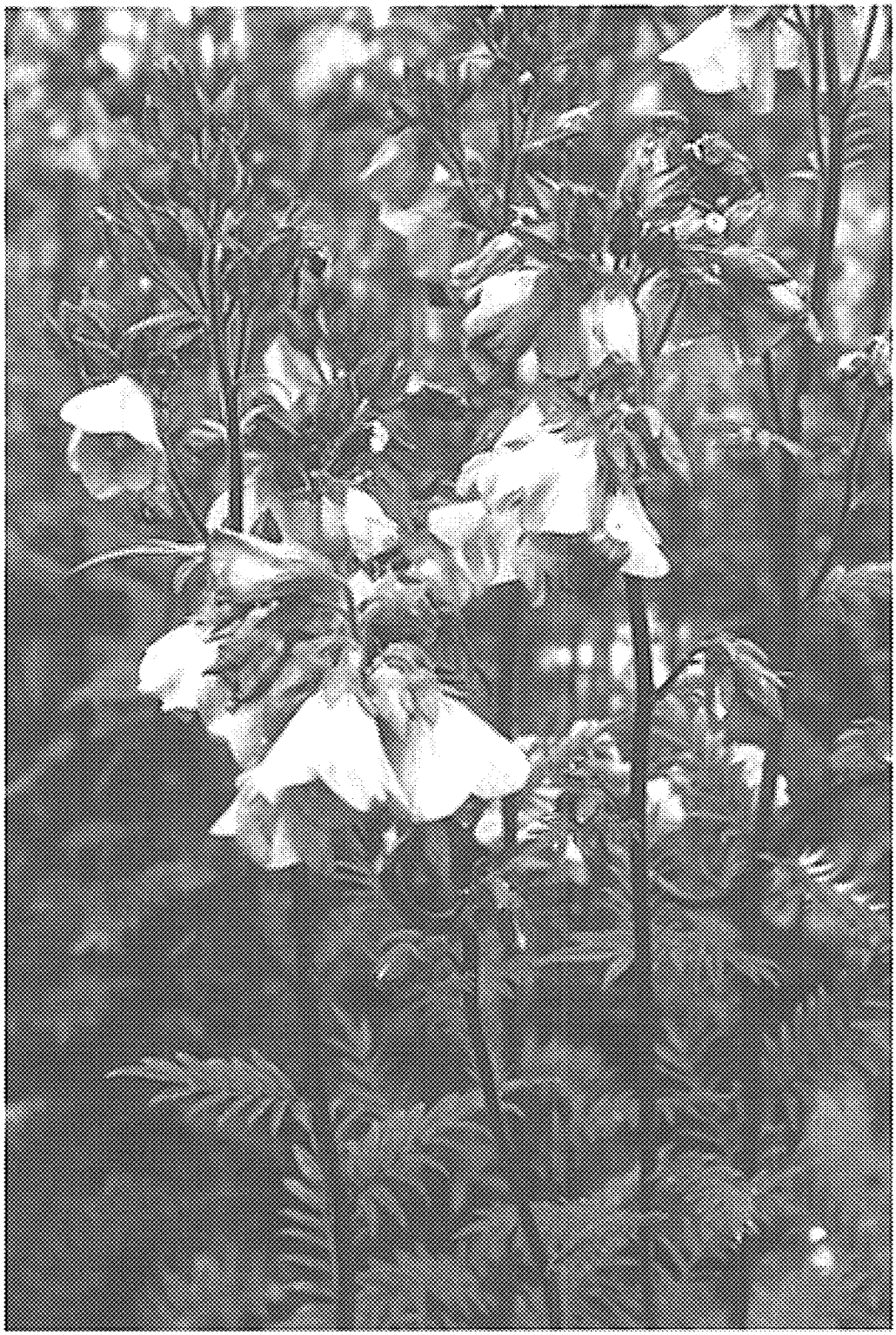

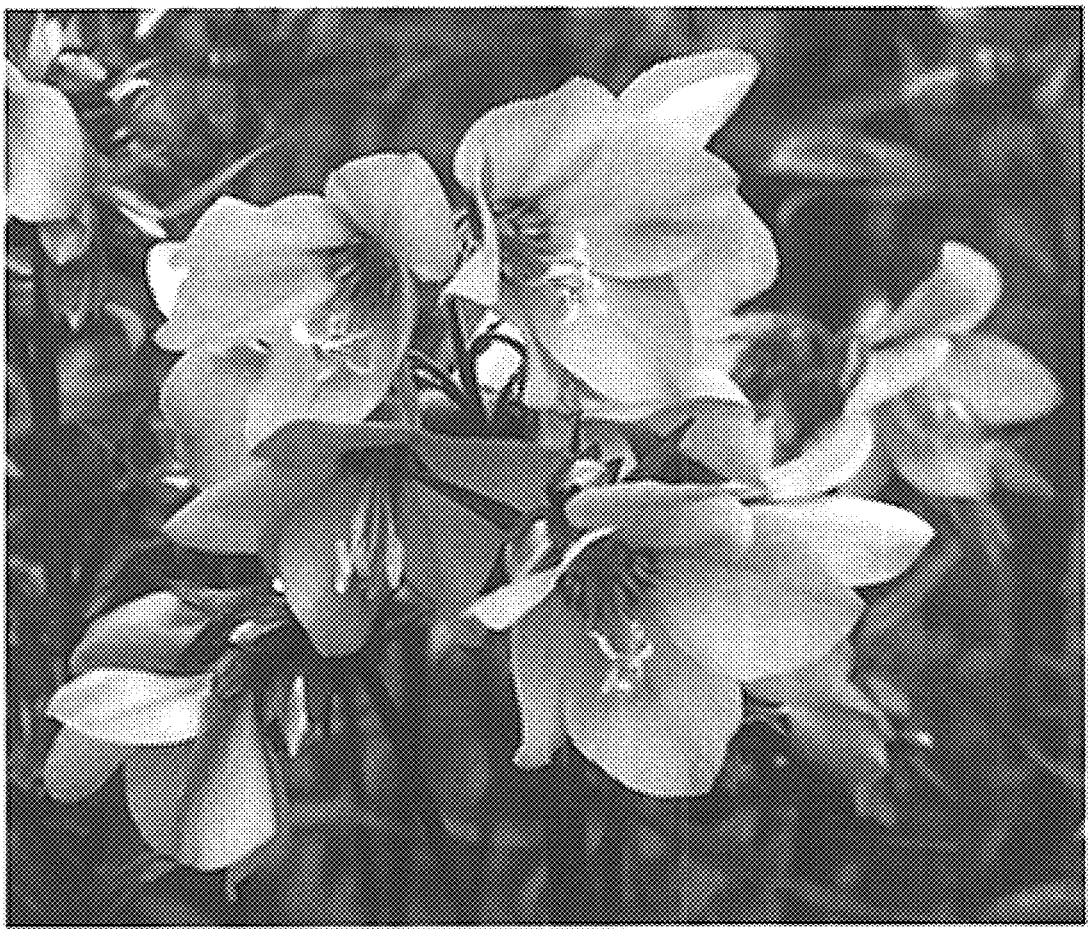

* * * * *